United States Patent [19]

Watanabe et al.

[11] Patent Number: 5,093,082
[45] Date of Patent: Mar. 3, 1992

[54] PURIFIED GUAIACUM RESIN AND METHOD FOR MAKING THE SAME

[75] Inventors: Masanao Watanabe, Tokyo; Kohji Kuroda, Chofu; Yoshiko Fujita, Tokyo, all of Japan

[73] Assignee: Dai Nippon Insatsu Kabushiki Kaisha, Tokyo, Japan

[21] Appl. No.: 242,690

[22] Filed: Sep. 9, 1988

[30] Foreign Application Priority Data

Aug. 17, 1988 [JP] Japan ................................ 63-204525

[51] Int. Cl.$^5$ ............................................. G01N 21/78
[52] U.S. Cl. ......................................... 422/56; 422/55; 422/57; 422/61
[58] Field of Search .................. 422/55, 56, 57, 61

[56] References Cited

U.S. PATENT DOCUMENTS 2,981,606 4/1961 Keston .
4,132,527 1/1979 Maekawa et al. .................... 422/56
4,297,271 10/1981 Guthlein et al. .

FOREIGN PATENT DOCUMENTS 61-247967 11/1986 Japan .
63-223095 9/1988 Japan .
63-223096 9/1988 Japan .

OTHER PUBLICATIONS

Chemical Abstracts 111:111979f, p. 363.
Chemical Abstracts 111:111980z, p. 363.
H. Auterhoff et al., "Arch. Pharmz.", pp. 618–626 (1966) and 302, pp. 545–554 (1969).

Primary Examiner—Christine Nucker
Assistant Examiner—Jeffrey Stucker
Attorney, Agent, or Firm—Birch, Stewart, Kolasch & Birch

[57] ABSTRACT

A purified guaiacum resin which is obtained by isolation from a natural guaiacum resin with chromatography using a gel for reversed chromatography as a stationary phase and a polar solvent as a mobile phase. The purified guaiacum resin does not contain substances causing the repellency of a specimen or constituents exhibiting unstable color development when it is used as a body fluid inspection agent and is subjected to color reaction in the presence of a peroxidase and hydrogen peroxide.

8 Claims, 2 Drawing Sheets

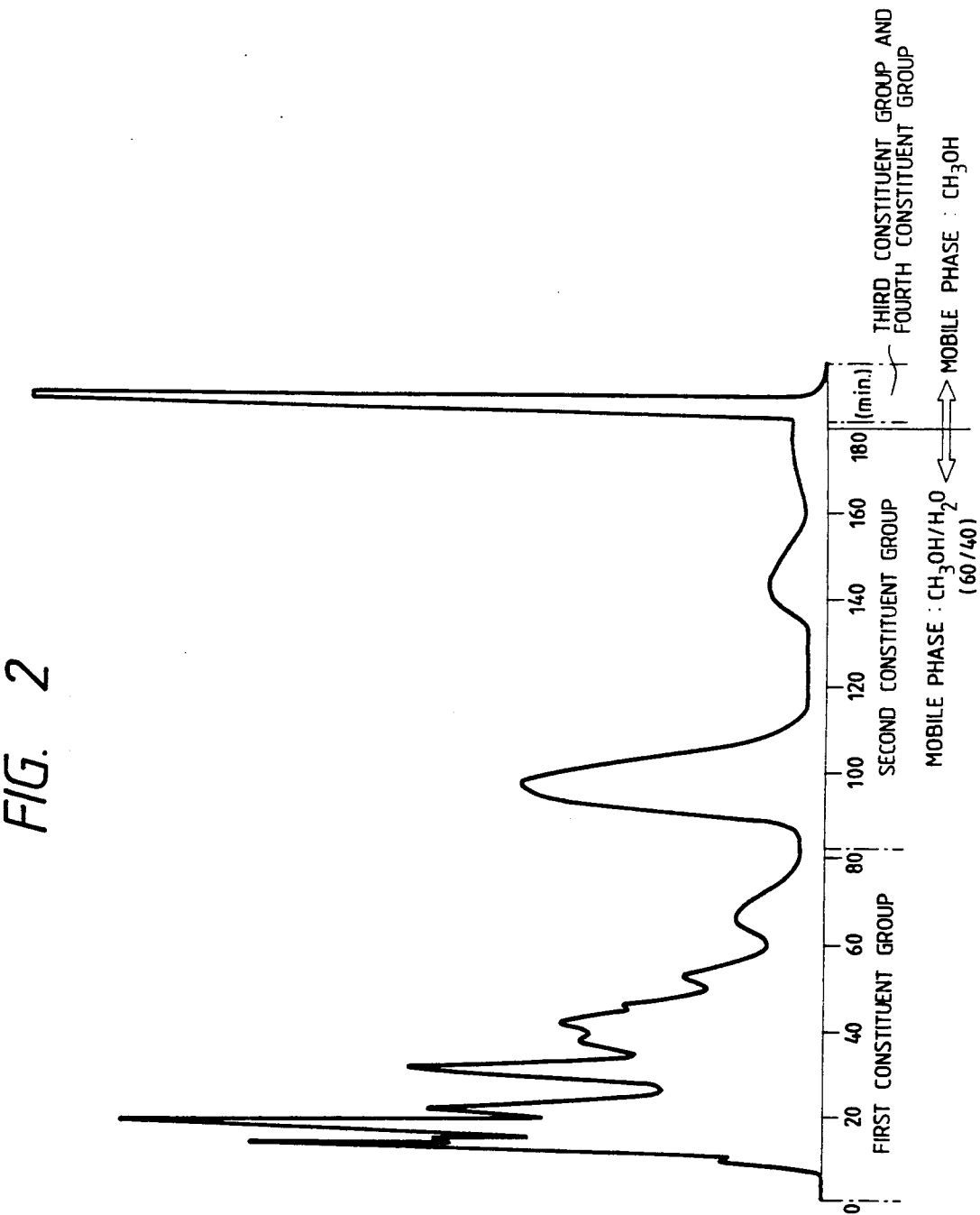

PURIFIED GUAIACUM RESIN AND METHOD FOR MAKING THE SAME

FIELD OF THE INVENTION

This invention relates to a purified guaiacum resin which is suitable for use as an oxidation-susceptible color indicator of a diagnostic agent for inspection of glucose and occult blood in body fluids and also to a method for preparing the same.

RELATED ART STATEMENT

For detection in early stages, diagnosis and control of diabetes, it is essential to rapidly and simply determine an amount of glucose in a body fluid such as urine, blood or lymph.

In prior detection of glucose in body fluids and particularly, urine, it is the common practice to use an inspection piece in which a glucose inspection reagent is impregnated in filter paper for judgement with a degree of color development of an oxidation-susceptible color indicator, or an inspection piece in which the reagent composition is applied onto a substrate. These inspection pieces or articles are advantageous from the standpoint of application in that the inspection operation is simple and the judgement can be made within a short time. In U.S. Pat. No. 2,981,606, there is described use of o-tolidine, guaiacum resin and o-phenylenediamine as an oxidation-susceptible color indicator of diagnostic agents which are used to detect glucose and occult blood in body fluids. Since benzidine compounds exhibit high detection sensitivity, o-tolidine has been predominantly used up to now. Although o-tolidine has high sensitivity, it is liable to discolor or lower in sensitivity during storage and a blue substance formed by the color reaction is unstable, so that a time for accurate reading becomes short, disenabling accurate judgement in practical applications. Thus, there is a demand for overcoming the drawback. The guaiac or guaiacum resin ordinarily employed as another oxidation-susceptible color indicator is a natural product and is collected from the heartwood of guaiac wood which is a tropical plant. Accordingly, the guaiacum contains a plurality of impurities other than constituents effective for coloration or color development, e.g. alpha-guaiaconic acid, beta-guaiaconic acid, guaiaretic acid, guaiacic acid, resene, gums, and essential oils and the like as is known in the art. In addition, the compositions of the effective constituents and the impurities are not always constant, thus making it difficult to ensure stable properties such as sensitivity and uniformity in color reaction. Several methods for purifying the guaiacum resin have been proposed. For instance, there is known a method in which when the guaiac is subjected to successive solvent extractions with petroleum ether, an ether and an alcohol, there is present in the ether-extracted fraction a constituent capable of developing a blue color in the presence of a peroxidase and hydrogen peroxide; and three main constituents are analytically obtained by isolation of the fraction with thin layer chromatography [(H. Auterhoff et al, "Arch. Pharmz." 299, pp. 618–626 (1966) and 302, pp. 545–554 (1969)]. In U.S. Pat. No. 4,297,271, it is stated that one of the above constituents has an Rf value of 0.45 in the thin layer chromatography (toluene/dioxane/glacial acetic acid 90:25:10) and can be industrially obtained by column chromatography using neutral silica gel and a mixture of n-heptane/acetic ester. This is described for elucidating a prior art technique. As described in the patent publication, the guaiac constituent obtained by the technique is not a single substance but is obtained as a mixing composition containing non-color-developing substances. From this, it is believed that because of the instability of the guaiacum resin constituent composition, the patent indicates the applicability of the composition at a level of examination of occult blood in the feces where a simple decision is made to qualitatively determine the presence or absence of occult blood. For using the guaiacum constituents as an inspection agent of high performance for glucose and occult blood in body fluids which requires semi-quantitative determination, the constituents should have a high sensitivity sufficient for color development at low concentrations and the capability of varying a developed color density in a stepwise manner over a range of from low to high concentrations. As is different from the case of the occult blood in the feces, with liquid specimens such as body fluids, a reagent layer containing an inspection agent has to be uniformly wetted with the specimen. In the method described in the U.S. Pat. No. 4,297,271 it is not possible to remove substances impeding the wetting properties from the guaiacum resin, with attendant vital drawbacks of color shading and the instability of an ultimate color density caused by the non-uniform deposition on or infiltration into the reagent layer of the specimen.

Moreover, the guaiacum resin contains constituent groups capable of developing a color but having Rf values of the thin layer chromatography different from the Rf value of 0.45. Among these groups, there are included constituents having different regions of color density. In order to cause quantitatively different color densities to develop over a wide range of concentration, it is necessary to contain these constituents. In this connection, however, according to the method described in the above patent, impurities are contained in large amounts since constituents covering a wide Rf value of from 0.2 to 0.6 are contained. Thus, purification is not substantially carried out. At least in an industrial sense, there is not known any method of recovering a constituent group effective as an oxidation-susceptible color indicator.

OBJECT AND SUMMARY OF THE INVENTION

The present invention contemplates to solve the above problems involved in the known color indicators and has for its object the provision of a purified guaiacum resin which is suitable as an oxidation-susceptible color indicator of a diagnostic agent for detecting glucose and occult blood in body fluids because color development-inhibiting substances have been removed therefrom and it contains substantially effective constituents. The invention also provides a method for preparing the purified guaiacum resin.

The present invention relates to a purified guaiacum resin which is obtained by isolation from a natural guaiacum resin with chromatography using a gel for reversed chromatography as a stationary phase and a polar solvent as a mobile phase. The purified guaiacum resin substantially does not contain color development-inhibiting substances causing the repellency of a specimen or constituents exhibiting unstable color development when it is impregnated in filter paper or applied to a substrate for use as a body fluid inspection agent and is subjected to color reaction in the presence of a peroxidase and hydrogen peroxide. In addition, the purified guaiacum resin contains a plurality of color-developing constituents capable of developing a color over a wide concentration range.

BRIEF DESCRIPTION OF DRAWINGS

FIG. 2 is a view showing an elution pattern of a crude guaiacum resin obtained by the use of an automatic collection-type chromatograph.

DETAILED DESCRIPTION OF PREFERRED EMBODIMENTS

Figure 1:
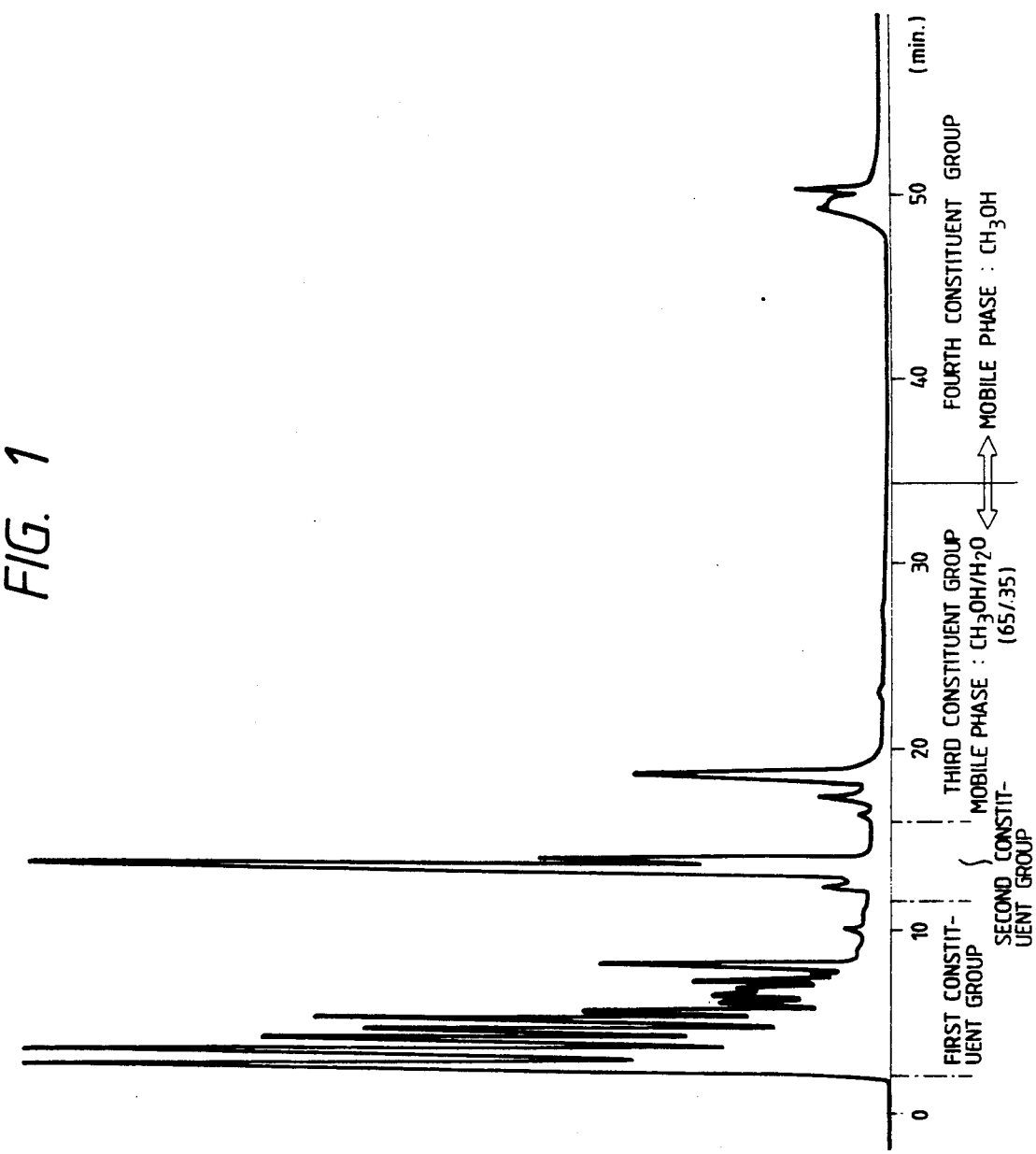
FIG. 1 is a view showing an elution pattern of a crude guaiacum resin separated by column chromatography.

The purified guaiacum resin according to the invention is obtained by subjecting a natural guaiacum resin to reversed chromatography using a fixed gel bed and an initial developing solvent of polarity higher than a solvent of water and methanol at a mixing ratio by volume of 1:9 to develop and eliminate a non-color developing constituent group including water-repellent constituents and an unstable color-developing constituent group from the guaiacum resin, collecting the resultant solution of a hydrophilic color-developing constituent group, and removing the solvent from the solution.

When the natural guaiacum resin is isolated according to the above method, four constituent groups are isolated. The first constituent group contains small amounts of color-developing constituents which are so small as not to be used in practical applications and also contains water-repellent constituents. Although it may be apparently curious that the first constituent group contains water-repellent substances, this is considered as follows: for the fabrication of an inspection article, the substances adsorb on polar carrier of the inspection articles so that the hydrophobic groups are oriented as arranged to be outward.

The second constituent group comprises reddish purple color-developing constituents and are unstable, and should be removed.

The third constituent group comprises a plurality of effective constituents capable of developing a deep blue color and is hydrophilic in nature.

The fourth constituent group comprises a mixture of constituents capable of developing a color in a wide range of concentration and contain color-developing constituents with high sensitivity although not relatively high in concentration. This group is hydrophilic.

The purified guaiacum resin of the invention consists of the third and fourth constituent groups among the above four groups. The present invention is described in more detail. In the preparation of the purified guaiacum resin, a natural guaiacum resin is first dissolved in acetone, to which toluene is added in order to remove a formed precipitate. The resultant filtrate is evaporated to dryness and the residue is dissolved in a polar solvent to obtain a crudely purified guaiacum resin. Examples of the gel for reversed chromatograph include an alkylated silica gel obtained by reaction of silanol groups on the surface of divided or spherical silica gel with an alkyl or aryl chlorosilane, a chemically combined silica gel, polymer-based alkylated hard gels, and the like. More particularly, there are mentioned alkylated silica gels such as of $C_{18}$, $C_8$, $C_4$, $C_2$, $C_1$ and the like, chemically combined silica gels with terminal groups such as $-NH_2$, $-CN$, phenyl and the like, and polymer-based alkylated hard gels such as of polymeric $C_{18}$ compounds. Although the elution time, more or less, varies depending upon the type of gel, little difference in the order of elution of the constituent groups is experienced, ensuring effective isolation of the groups.

The polar solvents useful in the present invention are selected from appropriate combinations of ethanol, methanol, ethanolamine, ethylene glycol, formamide, water, acetonitrile, dimethylsulfoxide, 1,3-dicyanopropane, diethyl ether, propyl chloride, ethyl acetate, propylamine, ethyl bromide, $CHCl_3$, tetrahydrofuran, methyl acetate, acetone, $CH_2Cl_2$, 1,2-dichloroethane, sodium octanesulfonate, dioxane, pyridine, benzonitrile, nitromethane, nitrobenzene and the like.

In some cases, up to 50% of non-polar solvents may be added to the polar solvent. For controlling the pH, acetic acid, trifluoroacetic acid, sodium octanesulfonate and the like may be used, but since they should be separated after elution, there is little chance of adding such materials except the case where they may be used as coexisting.

In the practice of the invention, the stationary and mobile phases as described before are used to separate by elution of the first and second constituent groups, which are color-inhibiting constituents, with an initial developing solvent. Subsequently, hydrophilic color-developing constituent groups useful for coloration are eluted. The initial developing solvent used for the separation of the inhibiting constituents is preferably one which has a polarity slightly higher than methanol. Examples of such solvent include mixed solvents of methanol and water, sodium octanesulfonate, acetic acid, trifluoroacetic acid and the like. All the mixed solvent should preferably have a polarity higher than that of a solution of methanol and water at a mixing ratio by volume of 9:1. The developing solvent used to collect the third and fourth constituent groups which are color-developing constituent groups is a solvent similar to the initial developing solvent. The third constituent group may be collected by means of the initial developing solvent as a constituent of a longer retention time. In practice, the third and fourth constituent groups can be eluted by the use of a solvent having a polarity smaller than the initial developing solvent. The elution with methanol alone or ethanol is effective.

The purified guaiacum resin obtained according to the invention is suitable as a color indicator of a test strip for the purpose of detecting glucose or occult blood in body fluids. It has been found that the guaiacum resin used for this purpose may contain not only the third and fourth constituent groups, but also constituents of a longer retention time than a fraction being eluted without involving any hindrance for achieving the above purpose.

The body fluid inspection article or piece may be made according to any known methods. For instance, an ordinary glucose detection composition obtained by formulating a color indicator, glucose oxidase, a peroxidase, a pH buffering agent, a water-soluble binder such as polyvinylpyrrolidone, and, if necessary, a humectant, a sensitivity regulator and a stabilizer is dissolved in water or a water-alcohol mixture, followed by impregnating the solution in a filter paper and drying the obtain a test strip. When the purified guaiacum resin of the invention is applied to the test strip, the uniformity of color development is improved.

Alternatively, a glucose detection dye containing ink composition in a non-aqueous solvent which has been proposed recently, is prepared by dissolving or dispersing in a non-aqueous solvent a color indicator, glucose oxidase, a peroxidae, a pH buffering agent, a binder and a water-absorptive powder. After addition of a humectant, a sensitivity regulator and a stabilizer to the composition, if necessary, the composition is applied onto a substrate and dried to obtain an inspection article for glucose detection. This article is better in sensitivity a d stability than the test strip of the type obtained by impregnation into filter paper. However, when the first constituent group is incorporated into the guaiacum resin used as the color indicator, water repellency is liable to appear, with the possibility of non-uniformity. This is considered as follows: when the non-aqueous solvent is evaporated for drying in the course of the fabrication of the inspection articles, the first constituent group locally gathers in the surface layer to impart water repellency. When the purified guaiacum resin of the invention consisting of the third and fourth constituent groups is used, the characteristic features of the guaiacum resin such as high sensitivity and good color stability are emphasized. The guaiacum resin is especially effective as the a non-aqueous solvent-based body fluid inspection article.

In the glucose inspection paper, the glucose in a body fluid reacts with oxygen in air by the action of a glucose oxidation enzyme such as glucose oxidase and is finally oxidized into gluconic acid and hydrogen peroxide. The resultant hydrogen peroxide produces nascent oxygen by the action of the peroxidase. This oxygen immediately reacts with the guaiacum resin to cause color development of the indicator. The presence or absence and the amount of the glucose in the body fluid can be semi-quantitatively determined in view of the degree of the color development. Accordingly, it is necessary that the body fluid allow the detection article to be uniformly wetted so that a density of the color can be judged over a wide range of from low to high concentrations and that the color tone be stably held after the color development. In this respect, the purified guaiacum resin of the invention exhibit good sensitivity, a wide color density range and good color stability. The purified guaiacum resin of the invention is effective not only for the above purpose, but also for detection of hydrogen peroxide and substances capable of producing active oxygen. The guaiacum resin can be widely employed in the fields of inspection agents such as in detection of reactions or semi-quantitative determination in the coexistence of glucose oxidase for glucose, urease for urea nitrogen, cholesterol oxidase for cholesterol, hemoglobin having the pseudo-peroxidase activity for occult blood and the like.

The present invention is described by way of examples, which should not be construed as limiting the invention.

EXAMPLE 1

Isolation of Purified Guaiacum Resin (1)

100 g of natural guaiacum resin was dissolved in 150 ml of acetone, to which 1.5 liters of toluene was added under agitation to remove the resultant precipitate (about 20 g) by filtration by suction. The resultant filtrate was concentrated in vacuum and dried to obtain about 70 g of a dried matter in this pretreatment. Part of the dried matter was dissolved in a mixed solution of methanol/water (65:35) to give a solution of 0.5 g/liter. This solution was once poured 20 μl and then the mixed solution of methanol/$H_2O$ (65:35) was passed at a rate of 0.5 ml/min at 40° C. into a column having a diameter of 4.6 mm and a height of 15 cm and containing oc- tadecylsilane-treated silica gel ($C_{18}$) which had been preliminarily equilibrated with a mixed solution of methanol/$H_2O$ (65:35). After confirmation of the elution of first and second constituent groups, a fraction consisting of a third constituent group was collected after a retention time of 16 minutes. After 32 minutes, the elution was facilitated by changing the moving bed to methanol to elute a fourth constituent group up to 60 minutes for collection. A detector made use of a UV ray with 280 nm.

FIG. 1 shows an elution pattern of a crude guaiacum resin separated by the column chromatography under the above conditions. The ordinate axis indicates an absorption of the UV ray at 280 nm and the abscissa axis indicates a retention time. In the FIG. 1, the first, second, third and fourth constituent groups are depicted as separated from one another. After the elution of the third constituent group, the mobile phase was changed to methanol and the resultant eluate was the fourth constituent group.

Preparation of Purified Guaiacum Resin (1)

In the same as in the Isolation (1), natural guaiacum resin was pretreated and 2 liters of a mixed solution of methanol/$H_2O$ (6:4) was added to about 70 g of the resultant dried matter.

80 ml of the solution was poured at room temperature into a column having a diameter of 5 cm and a height of 50 cm and containing octadecylsilane-treated silica gel ($C_{18}$) which had been equilibrated with a mixed solution of methanol/$H_2O$ (6:4), followed by passing 100 ml/minute of a mixed solution of methanol/$H_2O$ (6:4). After 180 minutes at which first and second constituent groups had been eluted, methanol was flowed to elute and collect a fraction until no absorption of a UV ray at 280 nm from a detector was observed. The elution pattern is shown in FIG. 2. The resultant purified guaiacum resin was developed under the same conditions as in the Isolation (1), whereupon it was confirmed that the first and second constituent groups were not detected but the resin consisted of the third and fourth ingredient groups. The amount of the collected resin was about 0.6 g.

Preparation of Purified Guaiacum Resin (2)

Natural guaiacum resin was pretreated in the same manner as in the preparation of Purified Guaiacum Resin (1). 2 liters of a mixed solution of methanol/$H_2O$ (11:9) was added to about 70 g of the resultant dried matter. This solution was preliminarily set in a high speed liquid chromatograph for collection and 100 ml of the solution was once poured at room temperature into a column having a diameter of 5 cm and a height of 50 cm and containing butyl-chemically combined silica gel ($C_4$) which had been equilibrated with a mixed solution of methanol/$H_2O$ (11:9), followed by passing 100 ml/minute of a mixed solution of methanol/$H_2O$ (11:9) to separate by elution of impurities. Thereafter, constituents contained in the column were eluted with ethanol. For detection, a UV ray with a wavelength of 280 nm was used. The fraction eluted with the ethanol was evaporated to dryness in an evaporator to obtain about 0.5 g of purified guaiacum resin (2).

Preparation of Purified Guaiacum Resin (3)

Natural guaiacum resin was pretreated in the same manner as in the Preparation of Purified Guaiacum Resin (1). 2.0 liters of a mixed solution of methanol/H$_2$O (6:4) was added to about 70 g of the resultant dried matter. 100 ml of the solution was once poured at room temperature into a column having a diameter of 5 cm and a height of 50 cm and containing octadecylsilane-treated silica gel (C$_{18}$) which had been preliminarily equilibrated with a mixed solution of 1.2 mM sodium octanesulfonate aqueous solution/H$_2$O (6:4), followed by passing 100 ml/minute or a mixed solution of 1.2 mM sodium octanesulfonate aqueous solution/H$_2$O (6:4) to separate by elution of impurities. Thereafter, constituents contained in the column were eluted with methanol. For detection, a UV ray with 280 nm was used. The fraction eluted with the methanol was evaporated to dryness in an evaporator to obtain about 0.5 g of purified guaiacum resin (3).

Preparation of Purified Guaiacum Resin (4)

Natural guaiacum resin was pretreated in the same manner as in the Preparation of Purified Guaiacum Resin (1). 2.0 liters of a mixed solution of methanol/H$_2$O (6:4) was added to about 70 g of the resultant dried matter. This solution was set in a high-speed liquid chromatograph for collection and 100 ml of the solution was once poured at room temperature into a column having a diameter of 5 cm and a height of 50 cm and containing butyl-chemically combined silica gel (C$_{18}$) which had been preliminarily equilibrated with a mixed solution of methanol/H$_2$O (6:4), followed by passing 100 ml/minute of a mixed solution of methanol/H$_2$O (6:4) to separate by elution of impurities. Thereafter, constituents contained in the column were eluted with acetonitrile/H$_2$O (6:4). For detection, a UV ray with 280 nm was used. The fraction eluted with the acetonitrile/H$_2$O was evaporated to dryness in an evaporator to obtain about 0.5 g of purified guaiacum resin (4).

Confirmation of Purified Guaiacum Resin

The first and second constituents and the third and fourth constituents collected according to the procedure of the Preparation of Purified Guaiacum Resin (1) were tested in the following manner. The groups containing the respective constituents were, respectively, developed on a silica gel-formed plate (F-254) with a mixed solution of toluene/dioxane/glacial acetic acid (90/25/10), over which an aqueous solution of peroxidase-H$_2$O$_2$ was sprayed. As a result, it was confirmed that among a plurality color bands of the crude guaiacum resin, a group of substances which assumed a reddish purple color and decolored within a short time after the coloration existed in the second constituent group. Further, a group of substances which assumed a blue color and were stable-after the coloration belonged to the third constituent group. A group of substances which were slightly low in color density but were able to develop a color in different ranges of concentration belonged to the fourth constituent group. The first constituent group was confirmed to contain only small amounts of color-developing substances. For the third and fourth constituent groups, the bands observed under the UV light were substantially coincident with color bands.

2 ml of a 10% H$_2$O$_2$ aqueous solution, 4 ml of ethanol and 50 mg of peroxidase of a horseraddish were charged into distilled water to make 9.9 ml of a solution. To the solution was added 0.1 ml of a solution of 2 mg of the purified guaiacum resin (1) in 20 ml of ethanol. 30 seconds after rapid mixing of the solutions, the mixed solution was subjected to measurement of a transmittance at 60 nm in a 1 cm cuvette to obtain a specific absorptivity, $E^{1\%}_{1cm}$, of 300.

Reference 1

Preparation of Purified-by-normal-phase Chromatography Guaiacum Resin 100 g of natural guaiacum resin was dissolved in 150 ml of acetone, to which 1.5 liters of toluene was added under agitation to filter the resultant precipitate (about 20 g) by suction. The resultant filtrate was concentrated in vacuum and dried to obtain about 70 g of a dried matter in this pretreatment.

500 ml of a mixed solution of n-heptane/acetic ester (2:5) was added to the dried matter while heating. 100 ml of the solution was added to a silica gel column (diameter 8 cm, height 70 cm) which had been preliminarily equilibrated with a mixed solution of n-heptane/acetic ester (2:5), followed by separation by elution with a mixed solution of n-heptane/acetic ester (2:5). 100 ml of the solution was used for each elution. The respective fractions were checked by thin layer chromatography to collect desired fractions, followed by concentration to 100 ml. The concentrate was mixed with 2 ml of n-hexane for recrystallization to obtain about 3.5 g of purified guaiacum resin. Confirmation of Purified-by-normal-phase Chromatography Guaiacum Resin:

The thus obtained purified guaiacum resin was developed on a silica gel-formed plate with a mixed solution of toluene/dioxane/glacial acetic acid (90:25:10), after which an aqueous solution of peroxidase-H$_2$O$_2$ was sprayed to cause a blue color to be developed, thereby obtaining an Rf value of 0.45.

Isolation of A First Constituent In Purified Guaiacum Resin 3 g of the purified-by-normal-phase chromatography guaiacum resin was added to and dissolved in 100 ml of a mixed solution of methanol/H$_2$O (6:4). The solution was set in a high-speed liquid chromatograph for collection and poured at room temperature into an octadecylsilane-treated silica gel (C$_{18}$) column equilibrated with a mixed solution of methanol/H$_2$O (6:4) and having a diameter of 5 cm and a height of 50 cm. Thereafter, a mixed solution of methanol/H$_2$O (6:4) was passed at a rate of 100 ml/minute to separate impurities by elution, followed by elution of a constituent retained in the column with methanol. For a detector, an UV ray of 280 nm was used.

The fraction of a short retention time (0–80 minutes) eluted with the mixed solution of methanol/H$_2$O (6:4) was evaporated to dryness in an evaporator to obtain about 1.0 g of the first constituent in the purified-by-normal-phase chromatography guaiacum resin. It was confirmed that when the purified-by-normal-phase chromatography guaiacum resin was isolated by the purifying method of the invention, the second constituent group (retention time: 80–160 minutes) was removed from the purified guaiacum resin eluted with methanol.

EXAMPLE 2

Fabrication and Evaluation of Performance of Inspection Articles For Detection of Glucose (1)

The purified-by-reversed-phase chromatography guaiacum resin obtained in Example 1 and the purifiedby-normal-phase chromatography guaiacum resin and the first constituent group alone thereof obtained in Reference 1 were mixed with an ink in amounts indicated below, thereby making inspection articles for detection of glucose. It will be noted that the purified guaiacum resins of Example 1 have little difference in performance and are merely referred to as purified-by-reversed-phase chromatography guaiacum resin.

TABLE 1

| | Mixing Ratio | |
|---|---|---|
| Inventive Product | purified-by-reversed-phase chromatography guaiacum resin (1) | 4.8 parts by weight |
| Control A | crude guaiac resin | 4.8 parts by weight |
| Control B | purified-by-normal-phase chromatography guaiacum resin | 4.8 parts by weight |
| Control C | purified-by-reversed-phase chromatography guaiacum resin and first constituent group | 4.8 parts by weight 1.6 parts by weight |
| Control D | purified-by-reversed-phase chromatography guaiacum resin and first constituent group | 4.8 parts by weight 4.8 parts by weight |

The guaiacum resins indicated in Table 1 were used and an ink composition of the following formulation for detection of glucose was finely dispersed by means of a homogenizer, followed by printing on a 300 micrometer thick white polystyrene sheet by screen printing in the form of a quadrilateral with each side of 5 mm. The screen plate used had a total thickness of a 80 mesh resist and a screen gauze of 130 micrometers. Ink composition for detection of glucose:

| | |
|---|---|
| Glucose oxidase (Grade II available from Toyobo) | 3.6 parts by weight |
| Peroxidase (Grade III available from Toyobo) | 2.4 parts by weight |
| Guaiacum resin | predetermined amounts (indicated in Table 1) |
| Sorbitan monolaurate (Span 20 available from Kao Co., Ltd.) | 7.2 parts by weight |
| L-ascorbyl stearate | 0.48 parts by weight |
| Citric acid | 2.8 parts by weight |
| Sodium citrate | 11.0 parts by weight |
| Polyvinylpyrrolidone (Kolidon 90, from BASF) | 12.6 parts by weight |
| Polyvinylbutyral (Eslek BX-1, from Sekisui Chem. Co., Ltd.) | 2.25 parts by weight |
| Fine cellulose powder (Avicel TG-D, from Asahi Chem. Co., Ltd.) | 171 parts by weight |
| n-Amyl alcohol | 228 parts by weight |
| Butylcellosolve acetate | 33.5 parts |

| | |
|---|---|
| | by weight |

The resultant print was dried at 60° C. for 40 minute, after which it was cut in the form of a flat dipstick to obtain an inspection article for detection of glucose.

Performance Test (1)

The inspection articles using the inventive product and the controls A, B, C and D were immersed in specimens of normal urine, and normal urine dissolving 25 mg/dl, 50 mg/dl, 100 mg/dl, 250 mg/dl and 500 mg/dl of beta-D-glucose and immediately removed from the specimens. The time required for coloration and a color tone at the inspection portion were checked for each article. The results are shown in Table 2.

TABLE 2

| Concentration of Glucose | Normal urine | 25 mg/dl | 50 mg/dl | 100 mg/dl | 250 mg/dl | 500 mg/dl |
|---|---|---|---|---|---|---|
| Inventive Product | — | +/20 sec. | ++/20 sec. | +++/20 sec. | ++++/20 sec. | +++++/20 sec. |
| Control A | — | — | — | +/1 min. | ++/1 min. | +++/2 min. |
| Control B | — | — | +/40 sec. | ++~+++/40 sec. | +++/40 sec. | +++++/40 sec. |
| Control C | — | — | +/40 sec. | ++~+++/40 sec. | +++/40 sec. | +++++/40 sec. |
| Control D | — | — | — | ++/1 min. | +++~++++/1 min. | +++++/1 min. |

(Color density +n/time before coloration)

The color tone in the Table was determined by comparison with a color table under a standard light source. The purified guaiacum resin of the invention is superior in sensitivity and coloration speed to the crude guaiacum resin and the guaiacum resins purified by the known method. It was found that the first constituent group which could be removed by the purification method of the invention lowered the sensitivity of the inspection article to a substantial extent.

After the inspection articles had been sealed in a glass container and stored at 40° C. for 12 months, they were tested in the same manner as described above. As a result, it was found that the inventive article and the controls B, C and D were uniform, clear and stable similar to those before the storage and could detect glucose in specimens in the same manner as before storage. However, when the control A was tested similarly, the coloration at the inspection reagent portion became poorer in uniformity and clearness as compared with that before the storage. It was difficult to determine a concentration of glucose in specimens. From this, it was confirmed that the second constituent group was an unstable constituent.

Performance Test (2)

The inspection sticks for detection of glucose using the inventive product and the controls A, B, C and D were each immersed in an aqueous solution dissolving 500 mg/dl of beta-D-glucose and immediately removed, followed by allowing to stand for 1 minute to check occurrence of color shading to such an extent of not less than 10% of the inspected portion. 100 sticks were subjected to measurement of a rate of occurrence of the color shading with the results shown in Table 3.

TABLE 3

|  | Inventive Product | Control A | Control B | Control C | Control D |
|---|---|---|---|---|---|
| Frequency of Occurrence of Color Shading | 2/100 | 51/100 | 15/100 | 9/100 | 27/100 |

From this, it was found that the removal of the first constituent group and the collection of the color constituents ensured good uniform characteristics.

gent portion was uniform and clear and the color density increased in a stepwise manner with an increase of the concentration of glucose in the specimen. Thus, the concentration of glucose in the specimen could be clearly judged within the above range. The colored inspection article was allowed to stand for 3 minutes with no change in color tone being recognized.

The purified-by-reversed-phase chromatography guaiacum resin in the composition was varied in the following manner, with the result that the color tone of the inspection portion and the time required for coloration were as follows.

TABLE 4

|  | Glucose Conc. | Normal | 50 mg/dl | 100 mg/dl | 250 mg/dl | 500 mg/dl |
|---|---|---|---|---|---|---|
| Inventive Product: | purified-by-reversed-phase chromatography guaiacum resin 0.96 parts by weight | — | +/30 sec | ++/30 sec | +++/30 sec | +++/30 sec |
| Control E: | purified-by-normal-phase chromatography guaiacum resin 0.96 parts by weight | — | +/40 sec | ++/40 sec | +++/40 sec | +++/40 sec |
| Control F: | crude guaiacum resin 0.96 parts by weight | — | — | +/40 sec | ++/40 sec | +++~++++/40 sec |
| Control G: | purified-by-reversed-phase chromatography guaiacum resin 0.96 parts by weight and first constituent group 0.32 parts by weight | — | +/40 sec | ++/40 sec | +++/40 sec | +++/40 sec |
| Control H: | purified-by-reversed-phase chromatography guaiacum resin 0.96 parts by weight and first constituent group 0.96 parts by weight | — | — | +/40 sec | ++~+++/40 sec | +++/40 sec |

EXAMPLE 3

Fabrication and Evaluation of Performance of Inspection Articles for Detection of Glucose Inspection articles of the impregnation-in-filter type containing the purified-by-reversed-phase chromatography guaiacum resin obtained in Example 1 were fabricated in the following manner.

A filter paper (No. 526, from Toyo Filter Paper Co., Ltd.) was impregnated with a solution of the following formulation and dried at 60° C.

| | |
|---|---|
| Glucose oxidase (Grade II, available from Toyobo Ltd.) | 0.72 parts by weight |
| Peroxidase (Grade III, from Toyobo Ltd.) | 0.48 parts by weight |
| Purified-by-reversed-phase chromatography guaiacum resin | 0.96 parts by weight |
| Sorbitan monlaurate (Span 20, from Kao Co., Ltd.) | 1.44 parts by weight |
| L-ascorbyl stearate | 0.10 part by weight |
| Citric acid | 0.56 parts by weight |
| Sodium citrate | 2.20 parts by weight |
| Polyvinylpyrrolidone (Kodolin 90, from BASF) | 1.26 parts by weight |
| Ethanol | 30.0 parts by weight |
| Water | 70.0 parts by weight |

The dried filter was cut into 5 mm square pieces and bonded on a 300 micrometer thick white polystyrene sheet by means of a double-coated adhesive tape, followed by cutting into a stick to obtain an inspection article for detection of glucose. Normal urine, and normal urine dissolving beta-D-glucose at concentrations of 50 mg/dl 100 mg/dl, 250 mg/dl, 500 mg/dl and 2,000 mg/dl were provided as specimens, in which the sticks were immersed, immediately removed and allowed to stand for 1 minute to observe a color tone of the inspection reagent portion. The color of the inspection rea- There was no difference of sensitivity of the inspection articles of the controls E and G from that of the inventive product. However, it was found that the sensitivity of the inspection article of the control H which included a large amount of the first constituent group was lowered. The inventive product is substantially more excellent than the controls H and G in the sensitivity of the inspection because the inventive product is superior in coloration speed to the controls E and G.

EXAMPLE 4

Fabrication of Inspection Articles for Detection of Occult Blood

Among ingredients of the following composition for detection of occult blood, cumene hydroperoxide and 6-methoxyquinoline used as a sensitizer were microcapsuled with use of gum arabic, to which other ingredients were added, thereby obtaining a composition for occult blood. Subsequently, the composition was uniformly dispersed by means of a homomixer and printed on a 300 micrometer thick white polystyrene sheet by screen printing to form an inspection reagent portion in the form of a square with each side of 5 mm. After the printing, it was dried at 60° C. for 40 minutes. The screen ruling of a plate used for the printing was 80 mesh and the total thickness of a resist and a screen gauze was 130 micrometers. After drying, the sheet was cut into stick pieces for inspection.

COMPOSITION FOR OCCULT BLOOD

| | |
|---|---|
| Cumene hydroperoxide | 3.6 parts by weight |
| 6-Methoxyquinoline (these two encapsulated) | 1.0 part by weight |
| Gum arabic | 9.4 parts by weight |
| Purified guaiacum resin | 1.5 parts by weight |

-continued

| (Example 1-(1)) | |
|---|---|
| Citric acid | 0.56 parts by weight |
| Sodium citrate | 2.2 parts by weight |
| Laurylsulfate triethanolamine | 1.62 parts by weight |
| Polyethylene glycol | 2.52 parts by weight |
| Polyvinylbutyral (Eslek BX-1, from Sekisui Chem. Co., Ltd.) | 3.6 parts by weight |
| Cellulose fine powder (Avicel TG-D, from Asahi Chem. Co., Ltd.) | 22.4 parts by weight |
| n-Amyl alcohol | 39.7 parts by weight |
| Butylcellosolve acetate | 13.0 parts by weight |

The following four specimens were provided.
(1) Normal urine
(2) Urine containing 0.06 mg/dl of human hemoglobin (Sigma Co., Ltd.)
(3) Urine containing 0.15 mg/dl of human hemoglobin (Sigma Co., Ltd.)
(4) Urine containing 0.75 mg/dl of human hemoglobin (Sigma Co., Ltd.)

The inspection test pieces were immersed in the above specimens (1) to (4) and immediately removed, followed by allowing to stand for 1 minute to check the color of the inspection reagent portion.

The colors of the inspection reagent portions were uniform and clear and the color density increased in a stepwise manner with an increase of the human hemoglobin concentration in the specimens. The concentration of the occult blood in the specimen could be appreciably judged within the above range. The colored test pieces were allowed to stand for 5 minutes, after which no change in the color could be recognized.

The test pieces for the inspection were sealed in a glass container and preserved at 40° C. for 12 months, followed by testing in the same manner as described above. The color of the inspection reagent portion was uniform, clear and stable as before and the concentration of human hemoglobin in specimens could be clearly judged.

EXAMPLE 5

Fabrication of Inspection Articles for Detection of Urea Nitrogen

For detecting of urea nitrogen in serum, inspection articles were made in the same manner as in Example 2 except that the following ink composition for detection of urea nitrogen was used instead of the ink composition for detection of glucose.

Ink Composition for Detection of Urea Nitrogen

| Urease (Grade II, from Toyobo Ltd.) | 3.6 parts by weight |
|---|---|
| Peroxidase (Grade III, from Toyobo Ltd.) | 2.4 parts by weight |
| Purified guaiacum resin (Example 1-(1)) | 4.8 parts by weight |
| Sorbitan monolaurate (Span 20, from Kao Co., Ltd.) | 7.2 parts by weight |
| Citric acid | 2.0 parts by weight |
| Sodium citrate | 11.0 parts by weight |
| Polyvinylpyrrolidone (Kolidon, from BASF) | 12.6 parts by weight |
| Polyvinylbutyral (Eslek BX-1, from Sekisui Chem. Co., Ltd.) | 2.25 parts by weight |
| Cellulose fine powder (Avicel, from Asahi Chem. Co., Ltd.) | 171 parts by weight |
| n-Amyl alcohol | 228 parts by weight |
| Butylcellosolve acetate | 33.5 parts by weight |

The resultant inspection article was immersed in a serum obtained by centrifugal separation of the human blood and removed therefrom immediately after the immersion, and allowed to stand for about 1 minute to check, whereupon it was found that the reagent layer assumed a blue color. Upon comparison with a standard color comparison table, it was found that about 10 mg/dl of urea nitrogen was contained.

EXAMPLE 6

Fabrication of Inspection Article for Detection of Total Cholesterol

For detection of the total cholesterol in a serum, the general procedure of Example 2 was repeated except that an ink composition for detection of the total cholesterol was used instead of the ink composition of detection of glucose, thereby obtaining an inspection article.

Ink Composition for Detection of Total Cholesterol

| Cholesterol esterase (Grade III, from Toyobo Ltd.) | 1.6 parts by weight |
|---|---|
| Cholesterol oxidase (Grade III, from Toyobo Ltd.) | 1.6 parts by weight |
| Peroxidase (Grade III, from Toyobo Ltd.) | 2.4 parts by weight |
| Purified guaiacum resin (Example 1-(1)) | 4.8 parts by weight |
| Sorbitan monolaurate (Span 20, from Kao Co., Ltd.) | 7.2 parts by weight |
| Monosodium phosphate | 6.0 parts by weight |
| Disodium phosphate | 9.0 parts by weight |
| Polyvinylpyrrolidone (Kolidon 90, from BASF) | 12.6 parts by weight |
| Polyvinylbutyral (Eslek BX-1, from Sekisui Chem. Co., Ltd.) | 2.25 parts by weight |
| Cellulose fine powder (Avice), from Asahi Chem. Co., Ltd.) | 171 parts by weight |
| n-Amyl alcohol | 228 parts by weight |
| Butylcellosolve acetate | 33.5 parts by weight |

The obtained inspection article was immersed in a serum obtained by centrifugal separation of an arbitrary human blood and removed therefrom immediately after the immersion, and allowed to stand for about 2 minutes. In was found that the reagent layer assumed a blue color, and the comparison with a standard color comparison table revealed that the serum contained a total cholesterol content of about 200 mg/dl.

According to the invention, passage through a column packed with a gel for reversed phase chromatography permits isolation and elution of impurities impeding color development and contained in natural guaiacum resin. By isolation and elution of constituent groups effective for color development of an inspection article which is used to the detection of glucose or occult blood in body fluids, a purified guaiacum resin containing constituents or ingredients capable of color development in a wide range of concentration can be obtained. In the practice of the invention, the separability is very good and re-utilization of the column is possible with good economy. Inspection articles using the purified guaiacum resin obtained according to the method of the invention for the purpose of detection of glucose and occult blood in body fluids are substantially free of any impurities impeding color development. Thus, the coloration during the course of diagnosis is clear. Moreover, since a plurality of color-developing constituents are contained, the color develops in high sensitivity and in a stepwise manner to a high concentration. The inspection article has high storage stability. Especially, when an inspection article is obtained by coating a non-aqueous composition onto a substrate, it ensures uniform color development and high sensitivity.

What is claimed is:

1. A body fluid inspection article comprising an inspection reagent layer formed on a substrate, said layer comprising a color indicator consisting of a purified guaiacum resin which contains a hydrophilic color-developing constituent group collected by providing a gel for reversed phase chromatography as a fixed bed, and subjecting a natural guaiacum resin to development with a solvent having higher polarity than a solvent of water and methanol at a mixing ratio by volume of 1:9 to eliminate initially eluted non-color-developing constituent group and color-developing unstable constituent group from said natural guaiacum resin.

2. A body fluid inspection article according to claim 1, wherein said inspection reagent layer is a layer for glucose inspection which is obtained by dissolving or dispersing said color indicator, a glucose oxidase, a peroxidase, a pH buffering agent, a binder and a water-absorptive powder in a non-aqueous solvent.

3. A body fluid inspection article according to claim 1 wherein said inspection reagent layer is a layer for glucose inspection which is formed by dissolving said color indicator, a glucose oxidase, a peroxidase, a pH buffering agent, and a water-soluble binder in water or a water-alcohol solution, impregnating the resultant solution in a filter paper, and drying the impregnated filter paper.

4. A body fluid inspection article according to claim 1, wherein said inspection reagent layer is a layer for occult blood inspection which is obtained by dissolving or dispersing said color indicator, an organic hydroperoxide, a sensitizer, a pH buffering agent, a binder and a water-absorptive powder in a non-aqueous solvent.

5. A body fluid inspection article according to claim 1, wherein said inspection reagent layer is a layer for urea nitrogen inspection which is obtained by dissolving or dispersing said color indicator, a urease, a peroxidase, a pH buffering agent, a binder and a water-absorptive powder in a non-aqueous solvent.

6. A body fluid inspection article according to claim 1, wherein said inspection reagent layer is a layer for total cholesterol inspection obtained by dissolving or dispersing said color indicator, a cholesterol oxidase, a peroxidase, a pH buffering agent, a binder and a water absorptive powder in a non-aqueous solvent.

7. An inspection article in the form of a test strip for inspection of a blood or urine sample, comprising an inspection reagent layer formed on a plastic or paper substrate, said layer comprising a color indicator consisting of a purified guaiacum resin which contains a hydrophilic color-developing constituent group collected by providing a gel for reverse phase chromatography as a fixed bed, and subjecting a natural guaiacum resin to development with a solvent having higher polarity than a solvent of water and methanol at a mixing ratio by volume of 1:9 to eliminate initially eluted non-color-developing constituent groups and color-developing unstable constituent groups from said natural guaiacum resin.

8. The inspection article of claim 7, wherein said purified guaiacum resin has a specific absorptivity, $E^{1\%}_{1cm}$, of about 300 to 600 nm after reaction with hydrogen peroxide and a peroxidase.

* * * * *